United States Patent [19]

Litzkow et al.

[11] Patent Number: 4,671,114
[45] Date of Patent: Jun. 9, 1987

[54] ACOUSTICAL DETECTION OF HIDDEN INSECTS

[75] Inventors: Carl A. Litzkow, Newberry; J. C. Webb; Shuichi Masuda, both of Gainesville, all of Fla.

[73] Assignee: The United States of America as represented by the Secretary of Agriculture, Washington, D.C.

[21] Appl. No.: 861,770

[22] Filed: May 9, 1986

[51] Int. Cl.[4] ............................................. G01N 29/04
[52] U.S. Cl. ........................................ 73/587; 73/591
[58] Field of Search ................. 73/587, 591, 584, 570; 340/573

[56] References Cited

U.S. PATENT DOCUMENTS 2,042,761  6/1936  Bennett ................................. 73/591
3,494,329  2/1970  Frieberger et al. .................... 73/584
4,562,736  1/1986  Iwasaki et al. ......................... 73/587

Primary Examiner—Anthony V. Ciarlante
Attorney, Agent, or Firm—M. Howard Silverstein; David G. McConnell; Raymond C. Von Bodungen

[57] ABSTRACT

The sound created by moving and chewing of insect larvae infested inside an agricultural commodity is acoustically detected and amplified, and thereafter transduced into an electrical signal which is electrically amplified for observation.

16 Claims, 9 Drawing Figures

ACOUSTICAL DETECTION OF HIDDEN INSECTS

BACKGROUND

This invention relates to detecting hidden insects in agricultural commodities.

PRIOR ART

Each year enormous quantities of postharvest agricultural commodities are rendered unusable by insects. Government food regulations, good quality control for marketing, means for early warning of hidden insects for crop control and health protection all require a method for detecting hidden insects.

Heretofore, detection of hidden insect infestation has been accomplished by X-ray, chemical analysis, destruction of the commodity for visual inspection and more recently by recording vibrations with piezoelectric devices placed in contact with the commodity. All these methods have obvious drawbacks. Some are not only prohibitively expensive but are inefficient and result in the destruction of the commodity. Furthermore, piezoelectric detection includes problems of cable noise, antenna effect, 60 cycle hum and sensitivity to low-frequency vibration.

SUMMARY

In the present invention, movement or chewing sounds made by insect larvae inside agricultural commodities are acoustically detected and simultaneously acoustically amplified. Thereafter the sound is transduced into an electrical signal which is electrically amplified for observation. As used in the specification and claims, the term "observation" refers to observing by hearing, computing, recording, or viewing on an oscilloscope, for example. The apparatus of the present invention comprises at least one sound detecting and amplifying diaphragm directly contacting the commodity in order to detect and simultaneously amplify sound at the surface of the commodity, wherein the diaphragm partially or fully supports the commodity; a sound waveguide connected at one end to the diaphragm to support the diaphragm and to transmit sound waves from the diaphragm to the opposite end of the waveguide; a transducer at said opposite end to convert the sound waves into an electrical signal; and electric signal amplification means connected to the transducer to amplify the signal for observation.

It is therefore an object of the present invention to provide a method and apparatus to inexpensively, reliably, and non-destructively test for insect larvae inside agricultural commodities.

Another object is to provide a detection system which eliminates the problems associated with prior art piezoelectric sensing devices, including the problems of cable noise, antenna effect, 60 cycle hum and sensitivity to low-frequency vibration.

Other objects and advantages will be obvious from the following more detailed description and drawings.

DETAILED DESCRIPTION

Figure 1:
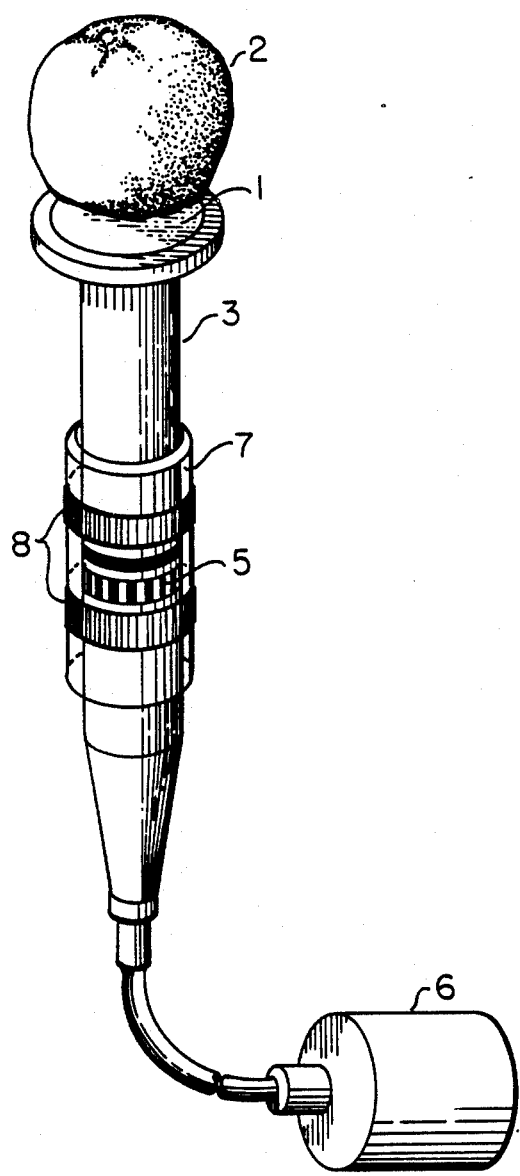
FIG. 1 is a perspective view of the device of the present invention in its simplest form.

The present invention is shown in its simplest form in FIG. 1. Reference numeral 1 designates a sound detecting-amplifying diaphragm directly contacting the surface of an agricultural commodity such as an orange 2. In addition to detecting the presence of larvae in the commodity, the diaphragm supports the commodity. A sound waveguide means 3 is connected at one end to the diaphragm to support the diaphragm and convey sound waves therefrom through the waveguide means. Any conventional bracket means, not shown, may be used to hold the diaphragm-waveguide means combination in place. The waveguide means is filled with a sound wave-conveying fluid such as air, although other sound-transferring fluids such as water or oil may be employed.

A transducer 5 such as a microphone is connected to the other end of waveguide means 3 to convert the sound waves to an electrical signal, which is subsequently amplified by a conventional electrical high-gain, low noise amplifier 6. Since fluid or air leaks in the waveguide means 3 may result in loss of sound waves transmitted to the transducer, an air-tight connection such as clear plastic tubing 7 and clamps 8 is provided where the transducer is coupled to the sound waveguide means. Other transducers such as a hyrophone may be employed rather than a microphone for liquid-filled versions.

As will be evident to those skilled in the acoustical arts, the dimensions and materials of construction of diaphragm 1 and waveguide means 3 may be varied in order to optimize amplification while reducing unwanted noise. For example, a larger diaphragm is able to affect more molecular movement of the air in the waveguide means 3 than a smaller one, given the same amount of linear diaphragm displacement. However, such a larger surface also may intercept more sounds that are not produced by the larvae, such as normal room noise or background conversation. Diaphragms having a diameter of about 1 to 1½ inches ordinarily will be suitable for most commodities.

The width, length and shape of the waveguide means 3 also contribute to the sound properties. While a simple waveguide means as shown in FIG. 1, i.e., a tube two inches long and one inch in diameter, will afford adequate detection for most commodities, such dimensions may be optimized for particular commodities.

The materials of construction for diaphragm 2 must be stiff enough to support the weight of the agricultural commodity being tested yet flexible enough to be responsive to very small amounts of sound energy at the surface of the commodity. Commercially available stethoscope diaphragms in most instances are suitable. Other diaphragm materials such as aluminum foil or thin, flexible, non-stretchable plastic used for example to make signs or cups also may be employed in the practice of the present invention.

Although some metals such as copper exhibit desirable acoustical properties for the diaphragm or waveguide means, plastics are preferred because of the elimination of noise from antenna effects, and the avoidance of metal corrosion due to acidic residues in some agricultural commodities especially citrus fruits. Furthermore, acidity of fruit, when combined with dissimilar metals, can cause ionic imbalance, resulting in crude diode or rectifier-detector action.

The shape of waveguide means 3 also affects the sound reproduction capabilities of the system. While waveguide means 3 may have the shape of a rigid-walled straight tube as shown in FIG. 1, it may be in the shape of a horn to maximize acoustical gain, for example. A tube with bends therein, as shown for example in FIG. 2a, also is suitable.

As will be evident to those skilled in acoustics, the diaphragm-waveguide means combination, besides amplifying the sound signal from the commodity, also alters the frequency of such sound. For example, while the frequency of the sound made by the chewing or moving of the larvae ordinarily may be 200-300 hertz or lower at the surface of a soft-skinned commodity, the frequency of such sounds at the output end of the waveguide means preferably should be about 1000-1500 hertz, to make such sounds more easily heard by the human ear, and easier to discriminate from the low frequency rumble typically found at most packing house environments. 60 cycle hum and multiples of 60 cycle also are greatly reduced. The appropriate diaphragm when combined with an 11-inch long, 1-inch diameter, air-filled plastic tube will produce such an increase with regard to detection in many soft-skinned fruits.

Figure 2B:
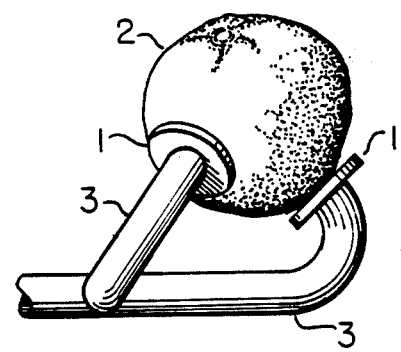
FIGS. 2a and 2b are front and top views, respectively, of a preferred embodiment.
Figure 2A:
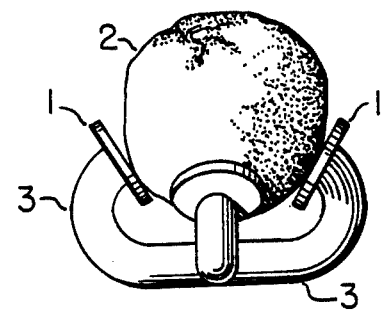

Referring now to the front and side views of the embodiment shown in FIGS. 2a and 2b, in this embodiment three diaphragm-waveguide means combinations are connected together so that a three-point support means is the sole support provided to hold a single, relatively large commodity, or to hold a nonsymmetrically shaped commodity, or to hold commodities which sometimes exist in a wide variety of sizes such as a grapefruit. Furthermore, the use of more than one diaphragm on a single test object enhances the ability of the apparatus to detect the presence of larvae in a large object, i.e., a plurality of diaphragms increases the probability of at least one of the sensors being in close proximity to the feeding or moving larvae inside the test object.

When using one or two diaphragms to hold and sense a single commodity, it may be necessary to provide support components in addition to the diaphragms in order to hold the commodity in place. For example, in the side and top views of the embodiment shown in FIGS. 3a and 3b, the combination of backstop 10 and diaphragm 1 are provided to hold a commodity 11 such as a walnut in place. Backstop 10 is an integral part of member 12 on which waveguide means 3 is firmly placed or secured.

Figure 4:
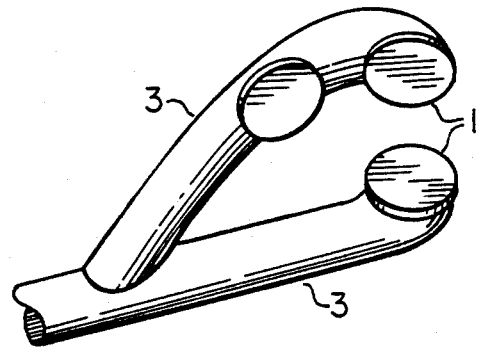
FIGS. 4, 5 and 6 are additional alternative embodiments.

In some configurations, more than one diaphragm 1 may be located on one of the individual waveguide tubes 3, such as shown in FIG. 4.

Figure 5:
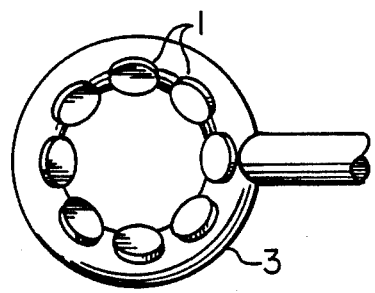

A still further embodiment is shown in FIG. 5 wherein waveguide means 3 is in the shape of a ring, and a plurality of diaphragms are located on the inner periphery of the ring. This embodiment is suitable for examining symmetrically rounded commodities such as grapefruits.

Figure 6:
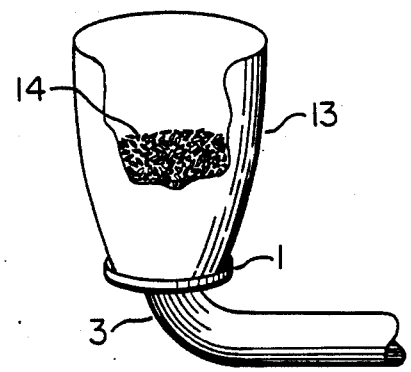

Yet another embodiment is shown in FIG. 6 wherein a container 13, the bottom wall of which is a diaphragm 1, is employed to detect the presence of larvae inside individual kernels of rice or grain 14. In tests to date with this embodiment, an infested kernel six inches away from the diaphragm in a quart of uninfested grain has been detected. Significant applications of this design include the detection of rice weavil, lesser grain borer, and Angoumais moth larvae in grain products.

Figure 7:
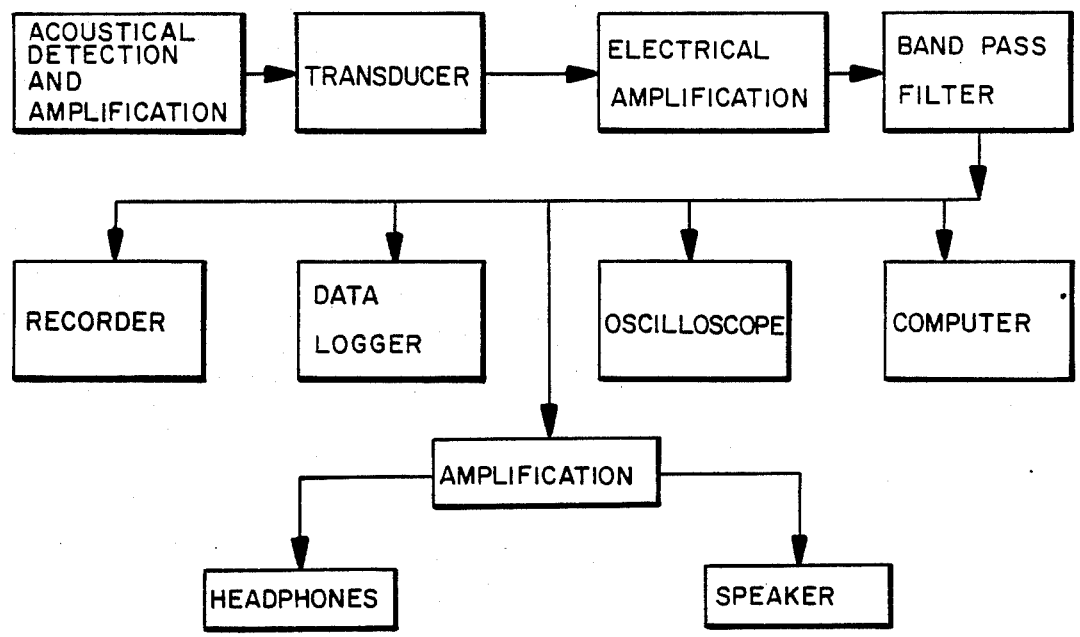
FIG. 7 is a schematic view of the entire system illustrating various types of observation means.

As shown schematically in FIG. 7, a preferred embodiment of the present invention is to employ a convential electrical signal variable band pass filter between the electrical signal amplifier and the signal observation means, to reject frequencies above and below those desired for observation. This figure also designates various kinds of observation means that may be employed in the practice of the present invention, i.e., an audio amplifier in combination with headphones or speakers; a slow-sweeping storage oscilloscope; a computer to quantify, record and gather data for biological studies; an event recorder; a data logger.

Figure 3A:
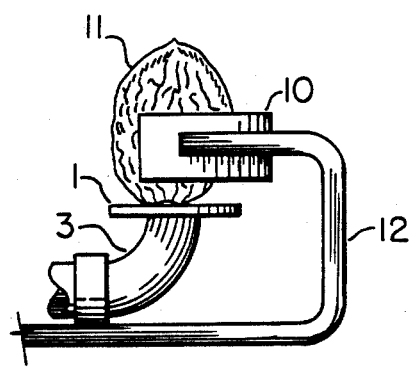
FIGS. 3a and 3b are side and top views, respectively, of an alternative embodiment.
Figure 3B:
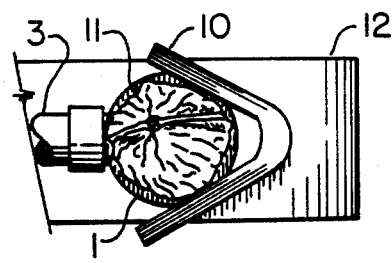

Any agricultural commodities which are susceptible to internal infestation by insect larvae may be tested by the system of the present invention. For example, grapefruits, cotton bolls, oranges, apples, nectarines, papayas, mangoes, citrus fruits may be examined. Individual grains of corn or wheat may be tested, especially in the apparatus of FIG. 6 wherein a mass of such kernels are placed in a container which includes a diaphragm as a wall thereof. Nuts such as walnuts or pecans may be examined, as shown in FIGS. 3a and 3b.

We claim:

1. An apparatus for detecting insect larvae in agricultural commodities comprising
    a. an agricultural commodity;
    b. means to hold said agricultural commodity, said holding means comprising at least one sound-detecting diaphragm:
    c. a sound waveguide means connected at one end to said diaphragm to support said diaphragm, and to convey sound waves through said waveguide means for said diaphragm:
    d. transducer means connected to the other end of said waveguide means to convert sound waves in said waveguide means to an electrical signal; and
    e. signal observation means connected to said amplifier means to observe the output of said amplifier means.

2. The apparatus of claim 1 further including band pass filter means between said amplifier means and observation means to filter out frequencies caused by unwanted background interference.

3. The apparatus of claim 1 wherein said diaphragm is the bottom wall of a container, and wherein said agricultural commodity is a batch of grain in said container.

4. The apparatus of claim 1 wherein there are a plurality of diaphragms on said apparatus.

5. The apparatus of claim 1 wherein said waveguide means is a rigid-walled tube.

6. A method for detecting insect larvae in agricultural commodities comprising
    a. accoustically detecting sound produced by movement or chewing of insect larvae infested inside an agricultural commodity;
    b. thereafter transducing the sound waves produced by said accoustical detection into an electrical signal;
    c. amplifying said electrical signal; and
    d. observing said amplified electrical signal.

7. The method of claim 6 further including filtering out unwanted frequencies created by background noise from said amplified electrical signal prior to observing said signal.

8. The method of claim 6 further comprising increasing the frequency of said sound waves to about 1000 to 1500 herz prior to transducing.

9. The method of claim 8 further including filtering out unwanted frequencies created by background noise from said amplified electrical signal prior to observing said signal.

10. The method of claim 6 further comprising holding said agricultural commodity of place by means of at least one sound-detecting diaphragm, wherein said diaphragm performs said accoustical detection step.

11. An apparatus for detecting insect larvae in agricultural commodities comprising
   a. means to hold a single object in place, wherein said object is an agricultural commodity, said holding means consisting essentially of a horizontally disposed sound detecting diaphragm, and a backstop adjacent thereto;
   b. a sound waveguide means connected at one end to said diaphragm to support said diaphragm, and to convey sound waves through said waveguide means from said diaphragm;
   c. a support member for said waveguide means, wherein said backstop is integral with said support member;
   d. transducer means connected to the other end of said waveguide means to convert sound waves in said waveguide means to an electrical signal.
   e. amplifier means connected to said transducer means to amplify said signal; and
   f. signal observation means connected to said amplifier means to observe the output of said amplifier means.

12. The apparatus of claim 11 further including an agricultural commodity held by said holding means.

13. An apparatus for detecting insect larvae in agricultural commodities comprising
   a. means to hold a single object in place, wherein said object is an agricultural commodity, said holding means consisting essentially of a plurality of sound detecting diaphragms;
   b. sound waveguide means connected to said diaphragms to support said diaphragms and to convey sound waves through said waveguide means from said diaphragms, wherein said waveguide means comprises a ring-shaped tube, and wherein said diaphragms are connected to the inner surface of said ring-shaped tube;
   c. transducer means connected to said waveguide means to convert said sound waves to an electrical signal;
   d. amplifier menas connected to said transducer means to amplify said signal; and
   e. signal observation means connected to said amplifier means to observe the out of said amplifier means.

14. The apparatus of claim 13 further including an agricultural commodity held in place by said holding means.

15. An apparatus for detecting insect larvae in agricultural commodities comprising
   a. means to hold a single object in place, wherein said object is an agricultural commodity, said holding means consisting essentially of three-point support means, wherein each of said points is a sound-detecting diaphragm;
   b. sound waveguide means connected to each of said diaphragms to support same, and to convey sound waves through said waveguide means from said diaphragms;
   c. transducer means connected to said waveguide means to convert said sound waves to an electrical signal;
   d. amplifier means connected to said transducer means to amplify said signal; and
   e. signal observation means connected to said amplifier means to observe the output of said amplifier means.

16. The apparatus of claim 15 further including an agricultural commodity held in place by said holding means.

* * * * *